(12) United States Patent
Charlez et al.

(10) Patent No.: US 11,213,651 B2
(45) Date of Patent: Jan. 4, 2022

(54) BIOFILM PREVENTION IN CATHETER SYSTEMS

(71) Applicant: Observe Medical ApS, Kongens Lyngby (DK)

(72) Inventors: Mikael Charlez, Mölndal (SE); Mikael Löfgren, Mölndal (SE)

(73) Assignee: Observe Medical ApS, Kongens Lyngby (DK)

( * ) Notice: Subject to any disclaimer, the term of this patent is extended or adjusted under 35 U.S.C. 154(b) by 597 days.

(21) Appl. No.: 16/083,155

(22) PCT Filed: Mar. 14, 2016

(86) PCT No.: PCT/EP2016/055469
§ 371 (c)(1),
(2) Date: Sep. 7, 2018

(87) PCT Pub. No.: WO2017/157416
PCT Pub. Date: Sep. 21, 2017

(65) Prior Publication Data
US 2019/0099583 A1 Apr. 4, 2019

(51) Int. Cl.
*A61M 25/00* (2006.01)
*A61M 39/16* (2006.01)

(52) U.S. Cl.
CPC ........ *A61M 25/0017* (2013.01); *A61M 39/16* (2013.01); *A61M 2025/0019* (2013.01)

(58) Field of Classification Search
CPC .............. A61M 25/0017; A61M 39/16; A61M 2025/0019
See application file for complete search history.

(56) References Cited

U.S. PATENT DOCUMENTS 6,436,084 B1 8/2002 Finch et al.
6,793,651 B1 * 9/2004 Bennett ................. A61F 5/4405
604/328

(Continued)

FOREIGN PATENT DOCUMENTS

CN 1448194 A 10/2003
CN 103861159 A 6/2014

(Continued)

OTHER PUBLICATIONS

English Language Translation of First Office Action and Search Report dated Jun. 16, 2020 from the China National Intellectual Property Administration for Chinese Application No. 201680083502. 2, 11 pages.

(Continued)

*Primary Examiner* — Benjamin J Klein
(74) *Attorney, Agent, or Firm* — RMCK Law Group, PLC

(57) ABSTRACT

Method for preventing biofilm formation on at least one luminal surface of a catheter system (1). The catheter system (1) comprises a collection vessel (4) and a tube (3) coupled to the collection vessel (4). The catheter system (1) comprises a catheter connector (2, 20, 200) coupled to the tube (3) and connectable to a catheter (6). The method comprises the consecutive steps of connecting the catheter connector (2, 20, 200) to the catheter (6) and supplying a silicon oil to an interior (25, 205) of the catheter connector. A catheter assembly comprising a catheter connector (20) comprising a port (24) providing access to the interior (25) of the connector and a dispensing unit (50) containing a silicon oil. A catheter connector (200) comprising a reservoir (207) containing a silicon oil and a releasing mechanism (208) releasing the silicone oil into the interior (205) of the connector.

15 Claims, 7 Drawing Sheets

(56) References Cited

U.S. PATENT DOCUMENTS

| | | | |
|---|---|---|---|
| 2005/0256447 A1* | 11/2005 | Richardson | A61M 5/16813 604/65 |
| 2008/0161763 A1* | 7/2008 | Harding | A61B 1/00188 604/265 |
| 2014/0228775 A1 | 8/2014 | Burkholz et al. | |
| 2016/0038070 A1 | 2/2016 | Charlez et al. | |
| 2018/0117279 A1* | 5/2018 | Yachia | A61L 29/16 |

FOREIGN PATENT DOCUMENTS

| | | |
|---|---|---|
| CN | 103957988 A | 7/2014 |
| CN | 105031752 A | 11/2015 |
| CN | 105120752 A | 12/2015 |
| CN | 204972644 U | 1/2016 |
| WO | 1984001721 A1 | 5/1984 |
| WO | 2003105942 A1 | 12/2003 |
| WO | 2008014447 A2 | 1/2008 |
| WO | 2014140328 A1 | 9/2014 |

OTHER PUBLICATIONS

PCT International Preliminary Report on Patentability dated Jun. 22, 2018 for PCT International Application No. PCT/EP2016/055469, 21 pages.

* cited by examiner

BIOFILM PREVENTION IN CATHETER SYSTEMS

CROSS-REFERENCE TO RELATED APPLICATIONS

This application is a 371 U.S. National Stage of International Application No. PCT/EP2016/055469, filed Mar. 14, 2016. The disclosure of the above application is incorporated herein by reference in its entirety.

TECHNICAL FIELD

The present invention relates to the field of catheter systems and the prevention of biofilm formation in such systems. In particular, the present invention relates to a method, a catheter assembly and a catheter connector for preventing biofilm formation on a luminal surface of a catheter system.

BACKGROUND ART

Urinary Tract Infection (UTI) is a very common nosocomial infection within the healthcare system today. The UTI extends length of stay, increase costs and contributes to an additional risk to the patients' health status. It is usually related to the installation of a urine catheter. It is revealed through clinical research that the risk of UTI increases by about 10% each day the catheter stays in the urinary tract. Bacteria has either their entrance from the outside of the body (about 64%) or from the very inside (about 36%). A majority of microbial infections are caused by biofilms that may form on a variety of surfaces. In addition to urinary tract infection also various other infections may be caused by biofilms, such as infection of blood. Infection of blood in the form of sepsis may have severe consequences.

WO 2014/140328 A1 discloses treatment of luminal surfaces of a urine handling system, in particular a measurement chamber of a urine measurement system, with an oil mixture comprising a silicon fluid in order to decrease degradation of the luminal surfaces in the form of encrustation.

In WO 84/01721 A1 it has been suggested to coat medical access systems, such as catheters and catheter adapters, by dipping in or spraying with an antimicrobial composition. The antimicrobial composition is prepared by mixing a resin, an antimicrobial metal and a solvent.

However, there is a need for an improved treatment procedure.

SUMMARY OF THE INVENTION

An object of the present invention is to obtain an improved treatment procedure preventing biofilm formation. An object of the present invention is to facilitate the treatment of a luminal surface of a catheter system. An object of the present invention is to improve the treatment of a luminal surface of a catheter system to prevent biofilm formation. An object of the present invention is to improve and simplify the handling of a catheter system preventing biofilm formation. An object of the present invention is to improve and simplify the treatment procedure and facilitate the handling associated therewith. An object of the present invention is to improve the effect of treatment of a luminal surface of a catheter system.

These and further objects are achieved by a method for preventing biofilm formation on at least one luminal surface of a catheter system as claimed in the independent claim 1, preferred variants thereof being defined in the associated dependent claims.

In the method according to claim 1 for preventing biofilm formation on at least one luminal surface of a catheter system, the catheter system comprises a collection vessel and a tube having a first end and a second end, wherein the first end of the tube is coupled to the collection vessel. The catheter system further comprises a catheter connector coupled to the second end of the tube and connectable to a catheter. The method comprises the consecutive steps of connecting the connector to the catheter and supplying a silicon oil to an interior of the connector.

The method of the present invention improves and simplifies a treatment procedure preventing biofilm formation. The method of the present invention facilitates the handling associated with the treatment procedure. The method of the present invention facilitates the handling of silicon oil, which is smudgy and slippery. The method of the present invention eliminates or at least reduces the contact with silicon oil during handling, since the silicon oil not is supplied until the connector is connected to the catheter. Thereby, the risk of contaminating clothes and surroundings with silicon oil is eliminated or at least reduced. The method of the present invention reduces the treated surfaces to the surfaces that are desirable to treat. The method of the present invention improves the connection of the catheter connection with the catheter, since the connection surfaces not are treated with silicon oil. The method of the present invention improves the effect of the silicon oil since the silicon oil may be applied shortly before use of the connector. Since the silicon oil may be applied shortly before use of the connector, the risk that the silicon oil is removed from the luminal surface is eliminated or at least reduced. The method of the present invention achieves a controlled treatment of luminal surfaces of a catheter system.

The above and further objects as well as the above advantages and effects are also achieved by a catheter assembly for preventing biofilm formation on a luminal surface of a catheter system as claimed in the independent claim 12, preferred variants thereof being defined in the associated dependent claim.

The catheter assembly according to claim 12 comprises a catheter connector connectable to a catheter and to a tube coupled to a collection vessel. The catheter connector comprises a port providing access to the interior of the connector. The catheter assembly also comprises a dispensing unit containing a silicon oil. The dispensing unit is adapted to be introduced into the port of the connector and to supply the silicon oil to the interior of the connector.

The above and further objects as well as the above advantages and effects are also achieved by a catheter connector for preventing biofilm formation on a luminal surface of a catheter system as claimed in the independent claim 14, preferred variants thereof being defined in the associated dependent claim.

The catheter connector according to claim 14 is connectable to a catheter and to a tube coupled to a collection vessel. The catheter connector comprises a reservoir containing a silicon oil. The catheter connector also comprises a releasing mechanism releasing the silicone oil into the interior of the connector upon activation of the releasing mechanism.

BRIEF DESCRIPTION OF THE DRAWINGS

The catheter system and the prevention of biofilm formation will now be described in more detail with reference to the drawings enclosed, in which examples of presently preferred embodiments of the invention are shown.

DETAILED DESCRIPTION

Figure 1:
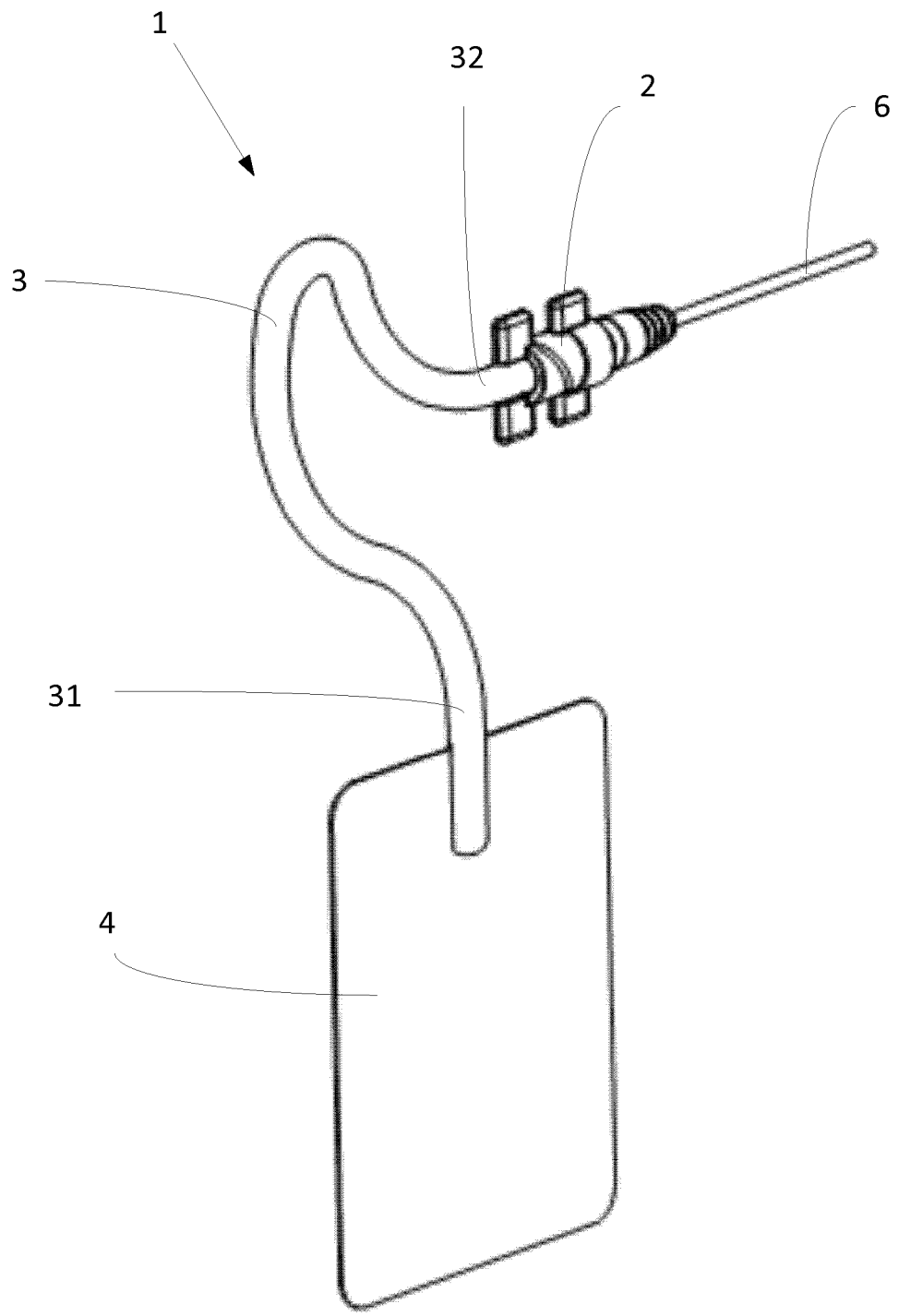
FIG. 1 is a perspective view of a catheter system according to the invention.

The present invention relates to prevention of biofilm formation on at least one luminal surface of a catheter system 1. A catheter system is visualized in FIG. 1.

The catheter system 1 comprises a collection vessel 4. The collection vessel 4 collects body fluid. The body fluid may be drained by means of a catheter 6 and collected in the collection vessel 4. The collection vessel 4 may be a collection bag 4.

The catheter system 1 comprises a tube 3. The tube 3 has a first end 31 and a second end 32. The tube 3 is coupled to the collection vessel 4. The first end 31 of the tube 3 is coupled to the collection vessel 4. The first end 31 of the tube 3 may be coupled directly to the collection vessel 4 or the first end 31 of the tube 3 may be coupled to a further device or container that is coupled to the collection vessel 4. The further device or container may for example be a measurement device e.g. measuring an amount of body fluid passing through the measurement device or a measurement chamber in which e.g. an amount of body fluid is measured. Body fluid present in the measurement chamber may be discharged into the collection vessel 4. The coupling of the first end 31 of the tube 3 to the collection vessel 4 may be fluid tight.

The catheter system 1 comprises a catheter connector 2, 20, 200. The catheter connector 2, 20, 200 is connectable to the tube 3. The catheter connector 2, 20, 200 is coupled to the second end 32 of the tube 3. The catheter connector 2, 20, 200 may be attached to the second end 32 of the tube 3. The catheter connector 2, 20, 200 may be affixed to the second end 32 of the tube 3. The catheter connector 2, 20, 200 may for example be glued to the second end 32 of the tube 3. The catheter connector 2, 20, 200 is preferably coupled directly to the second end 32 of the tube 2. The catheter connector 2, 20, 200 has an inlet 21, 201 and an outlet 22, 202. The outlet 22, 202 of the connector 2, 20, 200 is coupled to the second end 32 of the tube 3. The second end 32 of the tube 3 is coupled to the catheter connector 2, 20, 200. The coupling of the second end 32 of the tube 3 to the catheter connector 2, 20, 200 may be fluid tight.

The catheter connector 2, 20, 200 is connectable to a catheter 6. The catheter connector 2, 20, 200 may be adapted to be connected to a catheter 6. The catheter connector 2, 20, 200 may have an adaptor 23, 203 for connecting the connector 2, 20, 200 to a catheter 6. The adaptor may have a stepwise and/or conically increased circumference. The inlet 21, 201 of the connector 2, 20, 200 is connectable to a catheter 6.

The catheter connector 2, 20, 200 has an interior 25, 205. By the interior 25, 205 of the connector 2, 20, 200 is meant the hollow inside of the connector. The interior 25, 205 of the connector 2, 20, 200 includes the passage for body fluid from the inlet 21, 201 of the connector 2, 20, 200 to the outlet 22, 202 of the connector 2, 20, 200.

Figure 2:
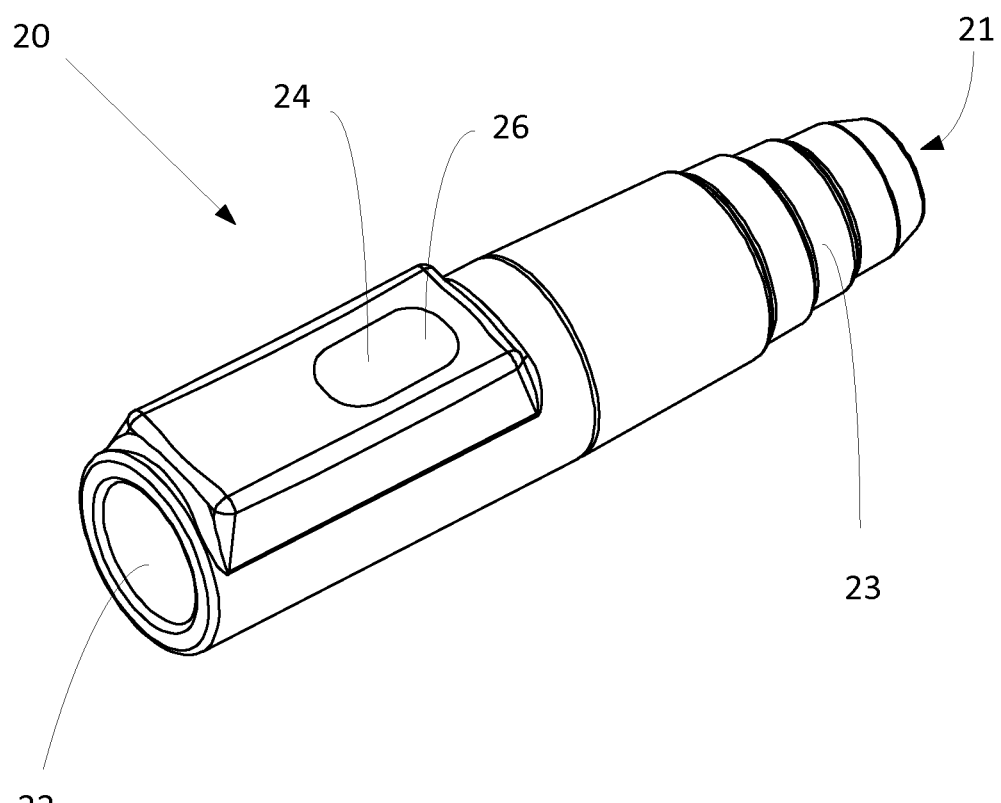
FIG. 2 is a perspective view of an embodiment of a catheter connector having a port according to the invention.
Figure 3:
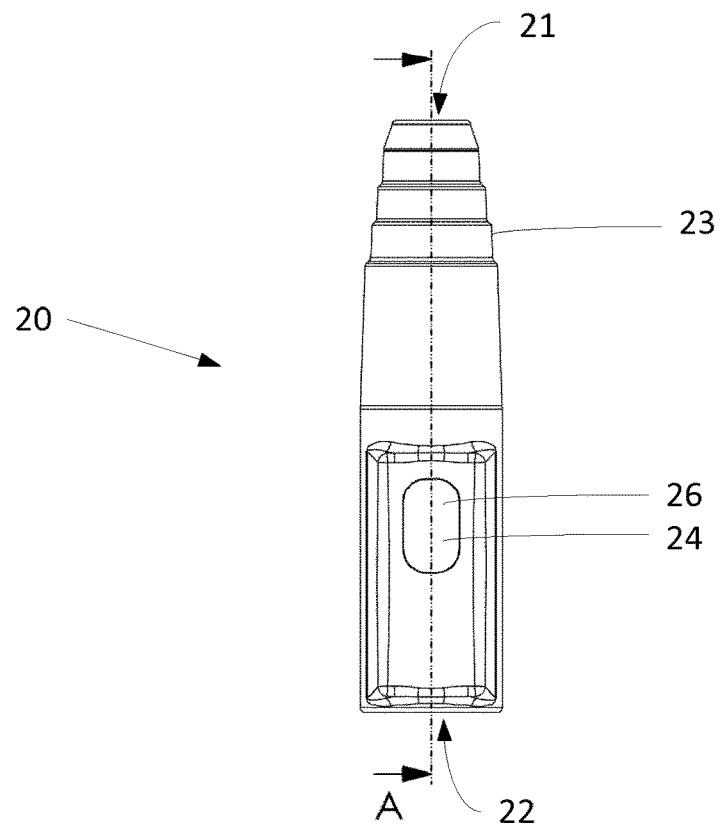
FIG. 3 is a top view of the embodiment of a catheter connector shown in FIG. 2.
Figure 4:
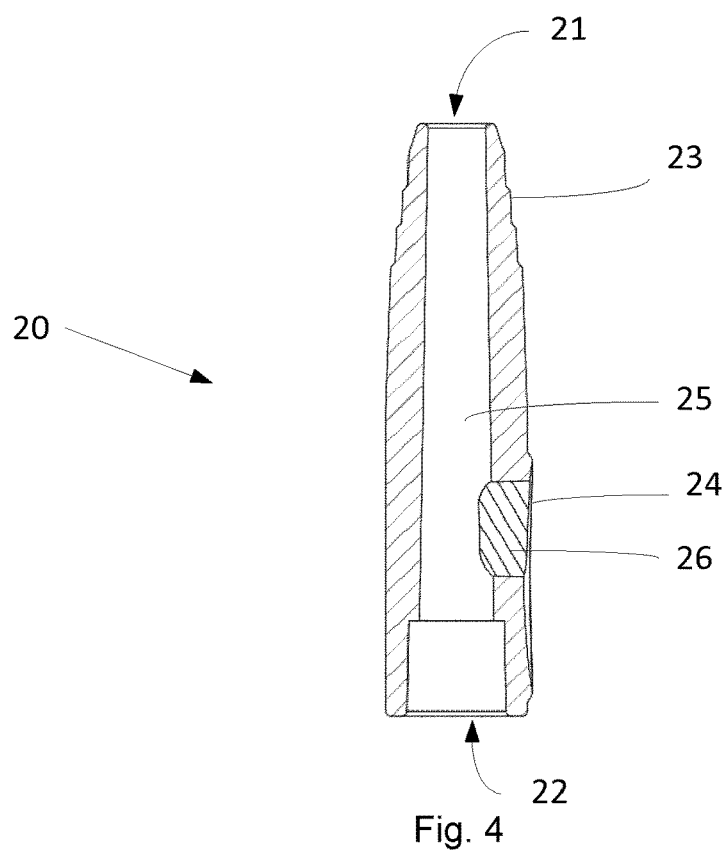
FIG. 4 is a cross sectional view of the embodiment of a catheter connector shown in FIGS. 2 and 3 along the section A-A of FIG. 3.
Figure 5:
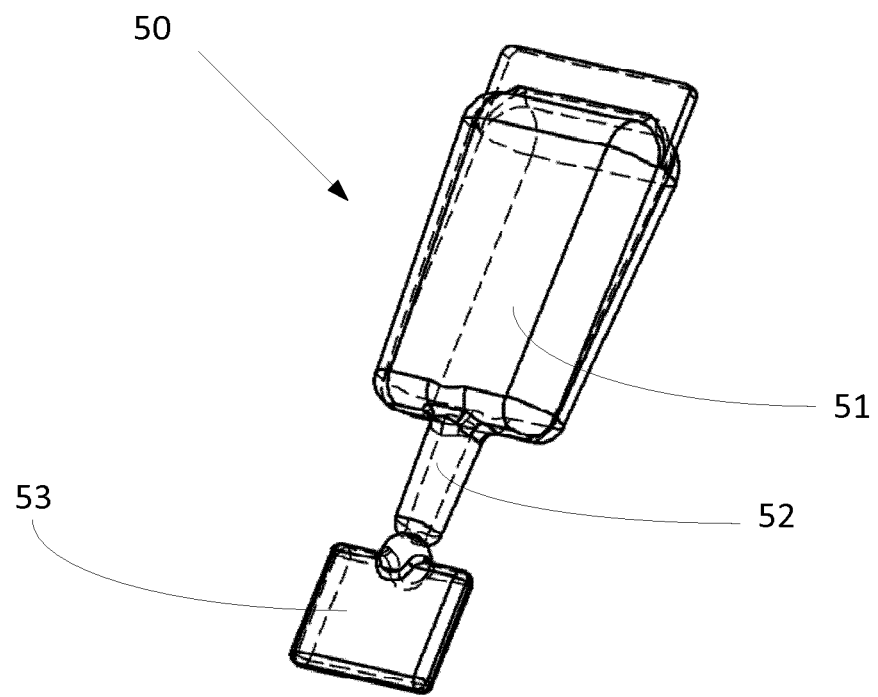
FIG. 5 is a perspective view of an embodiment of a dispensing unit according to the invention.
Figure 6:
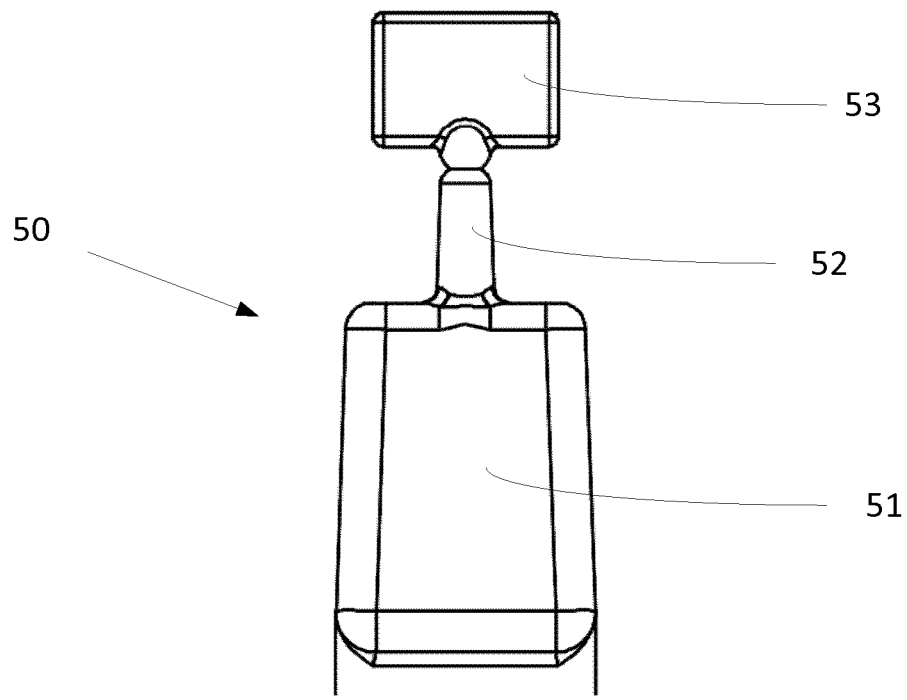
FIG. 6 is a front view of the embodiment of a dispensing unit shown in FIG. 5.
Figure 7:
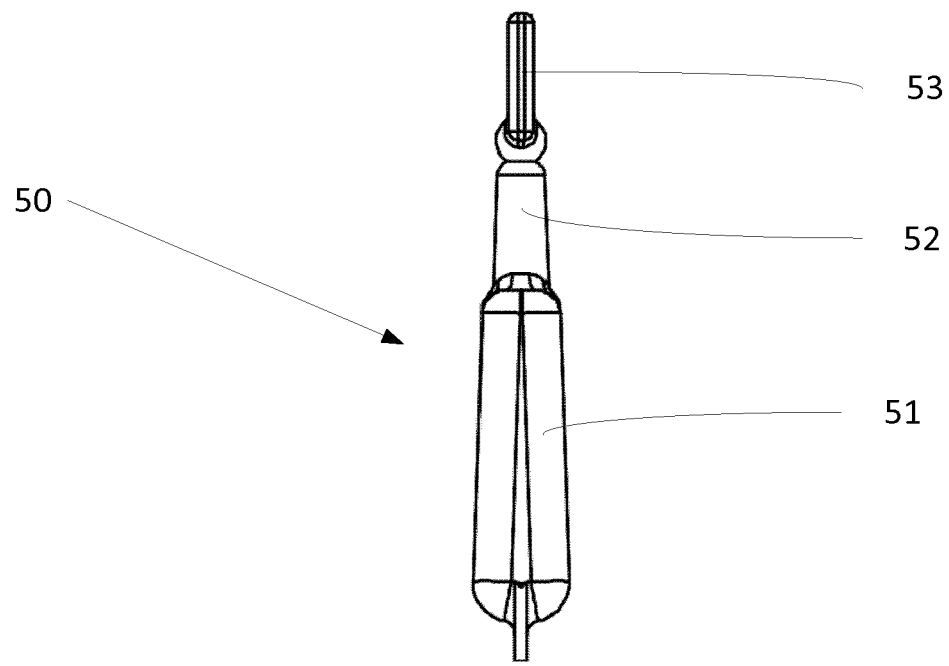
FIG. 7 is a side view of the embodiment of a dispensing unit shown in FIGS. 5 and 6.
Figure 8:
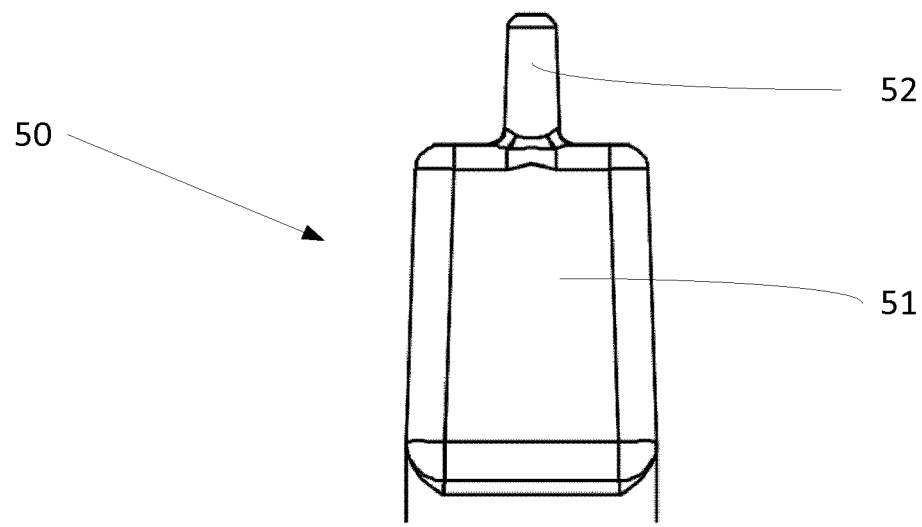
FIG. 8 is a front view of the embodiment of a dispensing unit shown in FIGS. 5-7 where a seal has been removed.

In one aspect, the catheter connector 20 comprises a port 24 providing access to the interior 25 of the connector 20. One such catheter connector is visualised in FIGS. 2-4. The port 24 may be an opening. The port may be provided in a wall of the connector. The port is sealable in order to prevent body fluid to leak out from the connector. The port may be provided with a valve. The valve seals the opening and provides access to the interior of the connector. The port 24 may be provided with one or more sealable membranes 26 that seals the opening and provides access to the interior of the connector. The membranes form a valve. The membranes may automatically provide access to the interior of the connector when a suitable object is inserted into the port. The membranes may automatically seal the opening when an object is removed from the port. The connector comprising a port may be a sample port connector, such as a needle-free sample port connector provided by Carmo A/S, article 09-795 or 09-796 (www.carmo.dk).

In one aspect, the silicon oil is contained in a dispensing unit 50. One version of a dispensing unit is visualised in FIGS. 5-8. The dispensing unit 50 is adapted to be inserted into the port 24 of the connector 20. By inserting the dispensing unit into the port, the silicon oil is easily transferred into the interior of the connector without or at least with reduced risk of spill or leakage of the silicon oil and there is no or a reduced risk of contaminating the surroundings, such as equipment, furniture and flooring, or clothes of persons handling the catheter system. The dispensing unit achieves a controlled supply of silicon oil. The amount of supplied silicon oil can easily be controlled by means of the dispensing unit. The amount of supplied silicon oil can easily be controlled by means of the dispensing unit for example by having the dispensing unit prefilled with a specific amount of silicon oil to be supplied or by grades on the dispensing unit assisting in the dispensing of a desired amount of silicon oil. The dispensing unit 50 may comprise a receptacle 51 containing the silicon oil. The dispensing unit is adapted to supply the silicon oil to the interior of the connector. A portion 52 of the dispensing unit 50 may be inserted into the port 24 such that the silicon oil can be transferred directly from the dispensing unit, such as from the receptacle 51 of the dispensing unit 50, to the interior 25 of the connector. The dispensing unit 50 may have a hollow tip 52 that is insertable into the port 24 of the connector 20. The hollow tip 52 communicates with the receptacle 51 containing the silicon oil. The hollow tip 52 has a channel through which the silicon oil is transferrable. The dispensing unit is adapted to dispense silicon oil. The dispensing unit may have a dispenser dispensing silicon oil from the dispensing unit, e.g. from the receptacle of the dispensing unit.

In one aspect, the dispensing unit 50 is a pipette 50 or a syringe. A dispensing unit in the form of a pipette is shown in FIGS. 5-8. A pipette 50 or a syringe has a tip 52 that is easily insertable into the port 24 of the connector 20. By inserting the tip 52 of the pipette 50 or the syringe into the port 24, the silicon oil can easily be transferred from the pipette 50 or syringe into the interior 25 of the connector 20. The silicon oil is easily transferred into the interior of the connector without or at least with reduced risk of spill or leakage of the silicon oil and there is no or a reduced risk of contaminating the surroundings or clothes. The tip 52 of the pipette 50 as well as the tip of the syringe is hollow and has a channel through which the silicon oil is transferrable. The dispensing unit 50 may be disposable. A pipette or a syringe can be inexpensive and can therefore be a suitable disposable article. The amount of supplied silicon oil can easily be controlled by means of the pipette or syringe for example by having the pipette or syringe prefilled with a specific amount of silicon oil to be supplied or by grades on the pipette or syringe assisting in the dispensing of a desired amount of silicon oil.

In one aspect, the silicon oil is prefilled in the dispensing unit 50. By prefilling the dispensing unit with the silicon oil, the dispensing unit, such as the pipette or syringe, contains the silicon oil before use of the dispensing unit. The dispensing unit is typically filled with the silicon oil when delivered to the user. The dispensing unit 50 may be provided with a seal 53 that seals the dispensing unit 50 such that the silicon oil is enclosed within the dispensing unit 50. The seal 53 is removed before use of the dispensing unit 50. The dispensing unit 50 is preferably a pipette 50. A pipette reduces the risk of mixing up the silicon oil dispensing unit with syringes intended for injection into the body and administration of medicaments. The pipette may be provided with a seal 53 that is removed before use of the pipette 50. The pipette 50 may be a sealed disposable pipette 50 prefilled with silicon oil, wherein the seal 53 is removed when the pipette 50 is to be used, i.e. when the pipette 50 is to be introduced into the port 24 and the silicon oil is to be transferred from the pipette 50 to the interior 25 of the connector 20. Also the syringe may be provided with a seal that is removed before use of the syringe. The spill and contamination risk is reduced by having a dispensing unit prefilled with silicon oil.

In one aspect of a dispensing unit in the form of a syringe, the syringe comprises a plunger. The silicon oil may be transferred from the syringe, such as from the receptacle of the syringe, to the interior of the connector by actuating the plunger.

In one aspect of a dispensing unit 50 in the form of a pipette 50, the silicon oil is transferred from the receptacle 51 of the pipette 50 by pressing on the receptacle 51 of the pipette 50. The silicon is thereby easily transferred form the pipette to the interior of the connector. A pipette is a convenient way of storing a transferring a suitable amount of silicon oil to the interior of a catheter connector having a port without spill and contamination. A specific amount of silicon oil can be prefilled in the pipette, e.g. the receptacle of the pipette, such that a desired amount of silicon is transferred into the interior of the catheter connector by pressing on the receptacle.

In one aspect, the dispensing unit 50 and/or the silicon oil is sterile. Thereby, the risk of infections is reduced. By having a sterile dispensing unit and/or silicon oil, the risk of introducing infectious substances to the inside of the catheter system is reduced. The handling is also facilitated, since disinfection of the dispensing unit is not necessary. The dispensing unit, preferably prefilled with the silicon oil, may be packed in a sealed packaging in order to preserve the dispensing unit sterile. The handling is thereby facilitated, since no cleaning of the dispensing unit, e.g. by disinfectant, is necessary.

The dispensing unit 50 may contain an amount of silicon oil suitable to be transferred into the interior of the connector for treatment of the luminal surface. The dispensing unit may comprise a predefined amount of silicon oil to be transferred to the interior of the connector for treatment of luminal surfaces of a catheter system. The receptacle 51 of the dispensing unit 50 may contain the suitable and/or predefined amount of silicon oil. The dispensing unit may contain 0.5-5 ml, such as 1-2 ml, silicon oil.

In one aspect, the catheter connector 200 comprises a reservoir 207 containing the silicon oil. One such catheter connector is visualised in FIGS. 9-11. This is an alternative to a catheter connector comprising a port and a dispensing unit containing the silicon oil. A reservoir containing the silicon oil comprised in the connector is a convenient way of having the silicon at hand. The spill and risk of contamination associated with handling of silicon oil is also eliminated or at least reduced. The amount of supplied silicon oil can easily be controlled by means of the reservoir. The reservoir 207 containing the silicon oil may be integrated in the connector 200.

In one aspect, the catheter connector 200 comprising a reservoir 207 also comprises a release mechanism 208 releasing the silicon oil to the interior 205 of the connector. This is visualised in FIGS. 9-11. The release mechanism 208 releases the silicon oil from the reservoir 207 and supplies the silicon oil to the interior 205 of the connector 200. The release mechanism is a convenient way of supplying the silicon oil to the interior of the connector. The reservoir and the release mechanism achieve a controlled supply of silicon oil.

In one aspect, the release mechanism 208 comprises an activator 209, 210 for operation of the release mechanism 208. The activator 209, 210 is accessible from the outside of the connector. One catheter connector having a release mechanism is visualised in FIGS. 9-11. Triggering the activator 209, 210 of the release mechanism 208 releases the silicon oil from the reservoir 207 to the interior 205 of the connector 200. The activator can activate the release mechanism and thereby release the silicon oil to the interior of the connector from the outside of the connector. The reservoir and the release mechanism eliminate or at least reduce the risk of contamination associated with handling of silicon oil.

Figure 9:
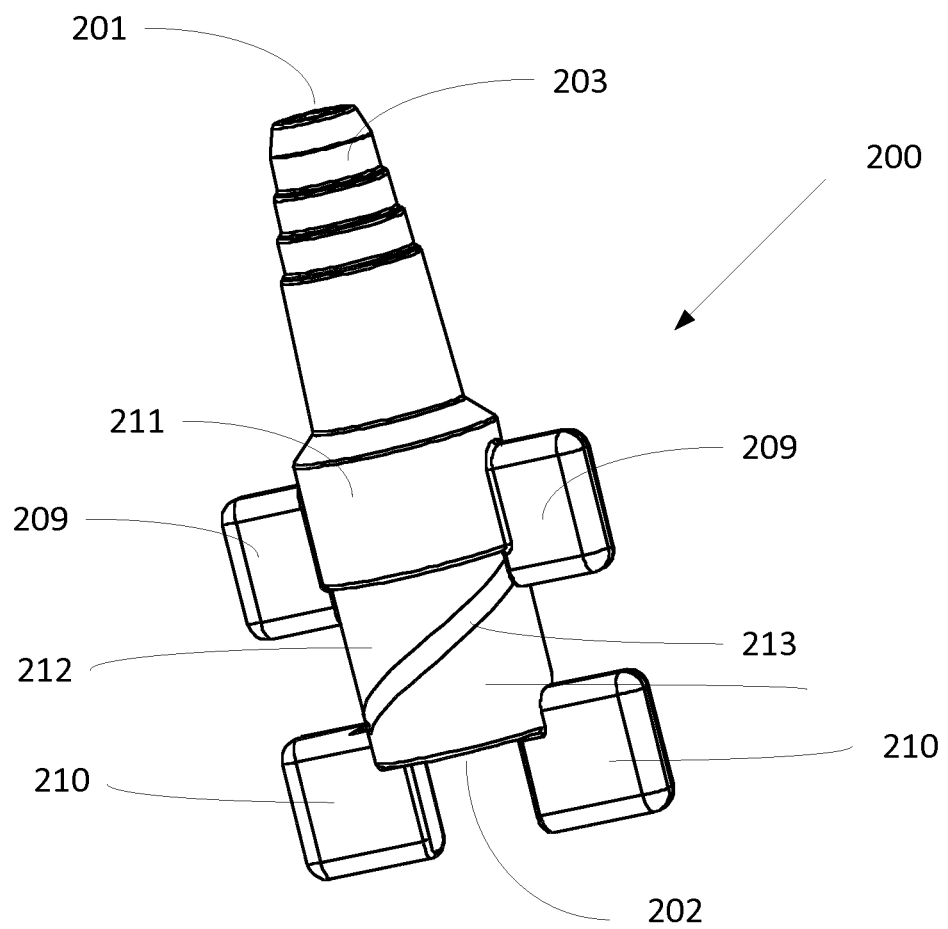
FIG. 9 is a perspective view of an embodiment of a catheter connector having a reservoir according to the invention.
Figure 10:
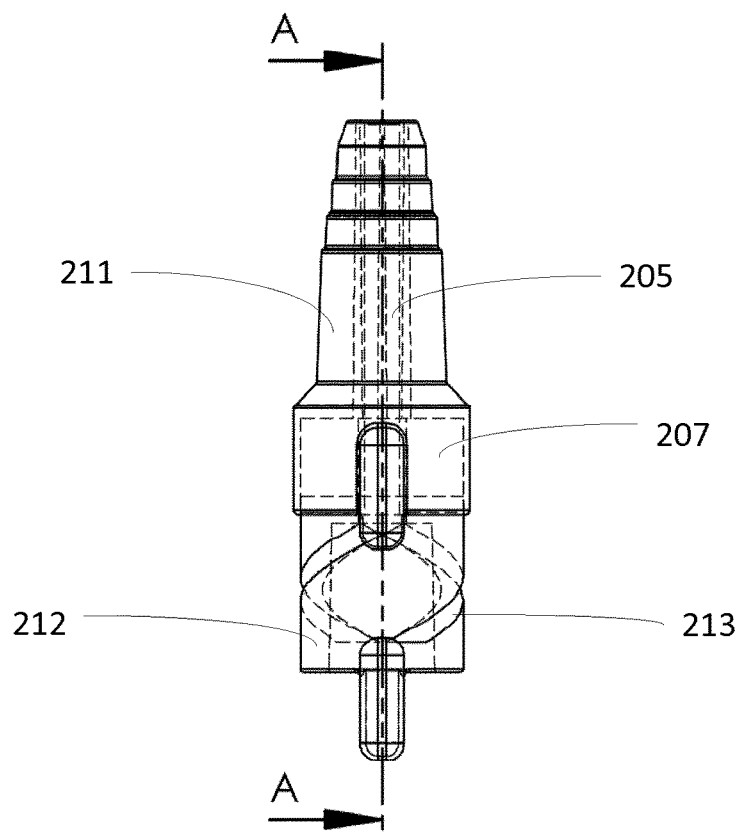
FIG. 10 is a side view with visualised inner contours of the embodiment of a catheter connector shown in FIG. 9.
Figure 11:
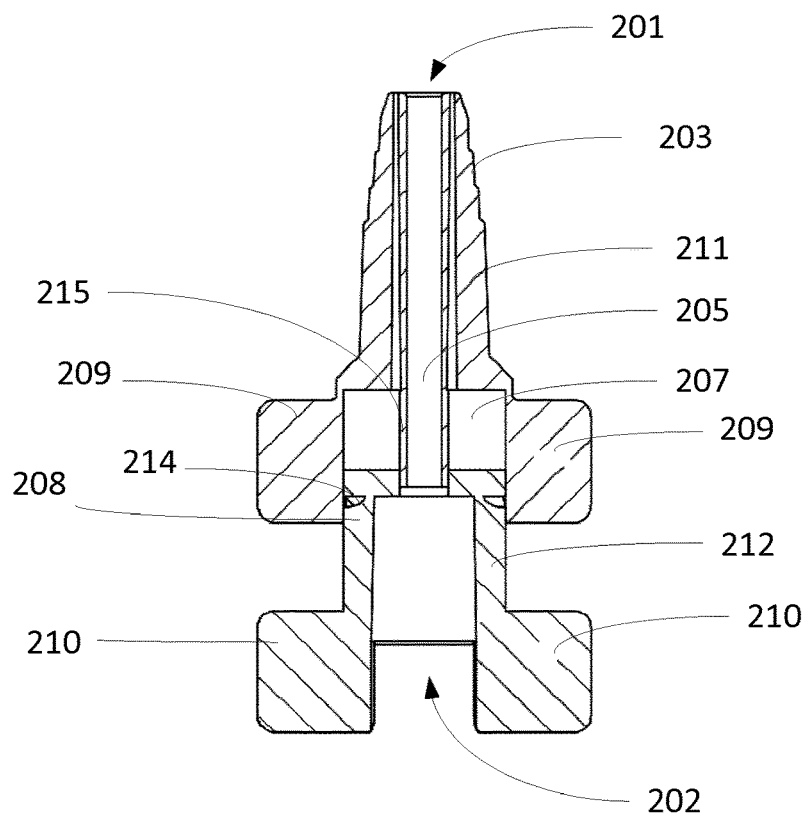
FIG. 11 is a cross sectional view of the embodiment of a catheter connector shown in FIGS. 9 and 10 along the section A-A of FIG. 10.

In one aspect, the connector 200 comprising a reservoir 207 also comprises a first connector part 211 and a second connector part 212 and the reservoir 207 is located between the first and second connector parts, see FIGS. 9-11. The second connector part 212 (or alternatively the first connector part) has a groove 213 in the form of at least a partial spiral. The first connector part 211 (or alternatively the second connector part if the first connector part has a groove) has a projection 214 mating with the groove. The projection 214 may be a single projection or a plurality of projections or an elongated projection in the form of at least a partial spiral for each groove. The groove and projection together forms a threaded connection between the first connector part 211 and the second connector part 212. The release mechanism is obtained by the first and second connector parts and the groove and projection thereof. Silicon oil contained in the reservoir is pushed out from the reservoir and to the interior of the connector when the connector parts are moved in relation to each other by means of the threaded connection. Silicon oil is pushed out from the reservoir to the interior of the connector through holes in an inner sleeve 215 delimiting the reservoir 207.

Each connector part 211, 212 may comprise a set of wings 209, 210 forming an activator. The release mechanism in the form of the threaded connection is operated by means of the activator in the form of the wings. By rotating the set of wings 209, 210 in relation to each other such that the second connection part 212 is screwed further into the first connection part 211 the volume of the reservoir 207 decreases and the silicon oil in the reservoir is pushed into the interior 205 of the connector 200. The reservoir is arranged between the first and second connection parts such that the silicon oil may be pushed into the lower end of the catheter when the second connection part is screwed further into the first connection part.

In one aspect, the release mechanism is activated when the catheter connector is connected to the catheter. The release mechanism may be automatically activated when the connector is connected to a catheter. The reservoir may comprise a membrane, such as s foil, that seals the reservoir and that is punctured, e.g. by a needle or pointed tip, when the connector is connected to a catheter.

In one aspect, the silicon oil is prefilled in the reservoir 207. By prefilling the reservoir of the connector with the silicon oil, the connector contains the silicon oil before use of the connector. The connector is typically filled with the silicon oil when delivered to the user. By having a prefilled connector reservoir, the handling of the silicon oil is facilitated. The spill and contamination risk is also reduced by having a connector reservoir prefilled with silicon oil.

In one aspect, the catheter connector 200 and/or the silicon oil is sterile. Thereby, the risk of infections is reduced. By having a sterile catheter connector and/or silicon oil, the risk of introducing infectious substances to the inside of the catheter system is reduced. The handling is also facilitated, since disinfection of the catheter connector is not necessary. The connector, preferably prefilled with the silicon oil in the reservoir, may be packed in a sealed packaging in order to preserve the connector sterile. The handling is thereby facilitated, since no cleaning of the connector, e.g. by disinfectant, is necessary.

The reservoir 207 of the connector 200 may contain an amount of silicon oil suitable to be transferred into the interior of the connector for treatment of the luminal surface. The reservoir of the connector may comprise a predefined amount of silicon oil to be transferred to the interior of the connector for treatment of luminal surfaces of a catheter system. The reservoir of the connector may contain 0.5-5 ml, such as 1-2 ml, silicon oil.

Silicone oil means a liquid polymerized siloxane with organic side chains. Silicone oil may be a compound with the general formula:

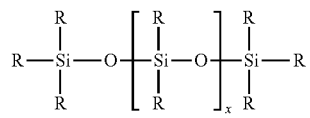

where each R can be an aliphatic group such as an alkyl group, for example a methyl, ethyl or propyl radical or alkoxy group or a phenyl group, or combinations thereof; and where x has a value of from about 0 to about 10,000, preferably from about 1 to about 200, and most preferably from about 10 to about 125. Silicone oil may be selected from the group of silicone esters. Silicone oil may be selected from the group of linear polydimethylsiloxanes.

In one aspect, the viscosity of the silicon oil is at most 600 cSt. The viscosity of the oil may be in the interval of 50 to 600 cSt, such as in the interval of 100 to 500 cSt.

The catheter system may be a system for a variety of body fluids, i.e. a biofluid originating from inside of a body of a living person. The body fluid may for example be urine, blood, exudate, pus, pleural effusion, lymph, gastric acid, abdominal fluid, spinal fluid, cerebral/spinal fluid or ascites. A preferred body fluid is urine.

As stated above, the present invention relates to a method for preventing biofilm formation on at least one luminal surface of a catheter system 1.

The method comprises the step of connecting the catheter connector 2, 20, 200 to a catheter 6. The inlet 21, 201 of the connector 2, 20, 200 may be connected to the catheter 6. The adaptor 23, 203 of the connector 2, 20, 200 may be connected to the catheter 6. The catheter connector may be connected to the catheter such that a fluid tight connection is established.

The method also comprises the step of supplying a silicon oil to an interior 25, 205 of the catheter connector 2, 20, 200. The connection step and the supplying step are performed consecutively, i.e. the step of connecting the catheter connector to the catheter is performed before the step of supplying a silicon oil to an interior of the catheter connector. Consequently, the supplying step of supplying a silicon oil to an interior of the catheter is performed after the connecting step of connecting the catheter connector to the catheter.

By supplying a silicon oil to the interior of the connector, the silicon oil is applied on a luminal surface of the catheter system. The silicon oil prevents biofilm formation as disclosed in WO 2014/140328 A1 and described in MacCallum, et al (Liquid-Infused Silicon As a Biofouling-Free Radical Material, ACS Biomater. Sci. Eng. 2015, 1, 43-51). Silicon oil is biocompatible and nontoxic or at least has low toxicity.

By firstly connecting the catheter connector to the catheter and then supplying the silicon oil, the silicon oil is only applied on the luminal surfaces in need of treatment. The outer surfaces of the catheter system, such as the outer surfaces of the catheter connector, the tube and the collection vessel, are not treated with silicon oil. Nor are the outer surfaces of the catheter treated with silicon oil. Further, the connection surfaces, i.e. the surfaces involved in the connection between the catheter connector and the catheter, such as the surfaces of the connector in contact with surfaces of the catheter and the surfaces of the catheter in contact with surfaces of the connector to establish the connection between the connector and the catheter, are not treated with silicon oil. If the connection surfaces are treated with silicon oil the risk that the catheter unintentionally is separated and disconnected from the catheter connection is increased due to the slippery characteristics of silicon oil. This is avoided by the invention. Only the luminal surfaces in need of treatment are treated with the silicon oil and no other surfaces such as outer surfaces and connection surfaces are treated. This increases the efficiency of the treatment since when supplying a specific amount of silicon oil all the silicon oil is applied on surfaces in need of treatment. The method controls the treatment of the luminal surfaces. By the method the surfaces to which the silicon oil is supplied and the time of supply is easily controlled.

Further, since the silicon oil is supplied after the catheter connector is connected to the catheter, there is no or at least a reduced risk of spilling or smudging silicon oil on equipment and clothes, which facilitates the handling of the catheter system.

The silicon oil may be applied on a luminal surface of the connector. The silicon oil may be applied on at least some of the luminal surfaces of the connector. Silicon oil is applied on some luminal surfaces and/or portions of a luminal surface of the catheter connector directly when supplied to the interior of the connector. Silicon oil may also be applied on portions of luminal surfaces of the tube, in particular upper portions of the tube, and/or lower portions of the catheter directly when supplied to the interior of the connector. Upper and lower portions are related to the flow direction of a body fluid. The body fluid flows from the catheter to the catheter connector and further through the tube to the collection vessel.

The silicon may be applied on further luminal surfaces of the catheter connector and/or on luminal surfaces located downstream of the catheter connector, such as luminal surfaces of the tube and luminal surfaces of the collection vessel, by means of the body fluid. The body fluid carries the silicon oil and brings the silicon oil in contact with the luminal surfaces further down along the flow path of the body fluid and thereby is silicon oil applied to the luminal surfaces downstream of the connector.

By luminal surfaces are meant inner surfaces, i.e. surfaces present on the inside. The luminal surface of the catheter system may be a luminal surface of the catheter connector, a luminal surface of the tube and/or a luminal surface of the collection vessel. The luminal surface may also be a luminal surface of a further device arranged along the flow path of a catheter system, such as a measuring device or a measurement chamber. The luminal surface may also be a luminal surface of a catheter.

The silicon oil may be applied on at least portions of the luminal surface. Thereby biofilm formation is prevented at least on portions of the luminal surface. The luminal surface may be at least partly coated with the silicon oil.

In one aspect, the method comprises the step of letting body fluid enter the catheter connector 2, 20, 200. The step of letting body fluid enter the catheter connector is preferably performed after the supplying step of supplying a silicon oil to an interior of the connector. However, as an alternative letting body fluid enter the catheter connector can also be performed before supplying of the silicon oil, e.g. may the step letting body fluid enter the catheter connector be performed continuously after the catheter connector has been connected to the catheter. Usually, the catheter is clamped, e.g. by a clamp, during catheterization. Body fluid may be let to enter the catheter connector by unclamping the catheter, such as by removing a clamp clamping the catheter. The step of letting body fluid enter the catheter connector may be performed by allowing body fluid to enter the catheter connector. Body fluid entering the catheter connector achieves application of the silicon oil on further surfaces of the connector and/or on luminal surfaces of the catheter system located downstream of the connector.

In one aspect, further silicon oil is supplied to the interior of the connector. The further silicon oil may be supplied after a period of use of the catheter system, such as after a period of use of about one day to about one month, such as after about one day to about two weeks, such as after about one day to about one week. Thereby, the treatment of the luminal surfaces is renewed and the preventive effect on biofilm formation is increased.

In one aspect of the method, wherein the catheter connector 20 comprises a port 24, the supplying step of supplying the silicon oil to the interior 25 of the catheter connector 20 is performed by first introducing the dispensing unit 50 into the port 24 and then transferring the silicon oil from the dispensing unit 50 to the interior 25 of the connector 20. The dispensing unit may be introduced into the port such that the silicon oil can be transferred directly from the dispensing unit to the interior of the connector. At least a portion of the dispensing unit may be inserted into the port such that the silicon oil can be transferred directly from the dispensing unit, such as from the receptacle of the dispensing unit, to the interior of the connector. The silicon oil may be transferred directly from the dispensing unit to the interior of the connector.

A suitable amount of silicon oil may be supplied to the interior of the connector for treatment of a luminal surface of the catheter system. The amount of silicon oil to be transferred to the interior of the connector may be predefined. A suitable and/or predefined volume of silicon oil may be about 0.5-5 ml, such as 1-2 ml.

In one aspect of the method, wherein the catheter connector 200 comprises a reservoir 207 containing the silicon oil and a release mechanism 208, the supplying step of supplying the silicon oil to the interior 205 of the catheter connector 200 is performed by activating the release mechanism 208 of the connector. Thereby, the silicon oil is released from the reservoir to the interior of the connector. Releasing the silicon oil from the reservoir of the connector to the interior of the connector by activating the release mechanism is a convenient way of supplying silicon oil to the interior of the connector without spill and contamination. Activation of the release mechanism achieves a controlled supply of silicon oil. The risk of contamination of surrounding and clothes with smudgy silicon oil is also reduced.

In one aspect of the method, wherein the release mechanism 208 comprises an activator 209, 210, the activation of the release mechanism 208 is performed by actuating the activator 209, 210. The activator 209, 210 is actuated from the outside of the connector 200. The risk of contamination with silicon oil is further reduced.

In one aspect, the release mechanism is activated when the catheter connector is connected to the catheter. The release mechanism may be automatically activated when the connector is connected to a catheter. The release mechanism may be automatically activated by puncturing a membrane when the connector is connected to a catheter.

The method and the steps and details comprised therein may in some aspects be as described above and have the features, effects and advantages as described herein.

As stated above, the present invention also relates to a catheter assembly for preventing biofilm formation on a luminal surface of a catheter system. The catheter assembly comprises the catheter connector 20 connectable to a catheter 6 and to the tube 3 coupled to the collection vessel 4, wherein the catheter connector 20 comprises the port 24 providing access to the interior 25 of the connector 20. The catheter assembly also comprises the dispensing unit 50 containing a silicon oil, which dispensing unit 50 is adapted to be introduced into the port 24 of the connector 20 and to supply the silicon oil to the interior 25 of the connector 20.

The catheter assembly and the parts comprised therein may in some aspects be as described above and have the features, effects and advantages as described herein. For example, the catheter assembly provides a controlled supply of silicon oil and reduces the risk of contamination of surroundings during handling of the catheter system. Also, the dispensing unit 50 may be a pipette 50 or syringe as described above.

As stated above, the present invention further relates to a catheter connector 200 for preventing biofilm formation on a luminal surface of a catheter system. The catheter connector 200 is connectable to a catheter 6 and to the tube 3 coupled to the collection vessel 4. The catheter connector 200 comprises the reservoir 207 containing a silicon oil and the releasing mechanism 208 releasing the silicone oil into the interior of the connector upon activation of the releasing mechanism 208.

The catheter connector and the parts comprised therein may in some aspects be as described above and have the features, effects and advantages as described herein. For example, the catheter assembly provides a controlled supply of silicon oil and reduces the risk of contamination of surroundings during handling of the catheter system. Also, the release mechanism may 208 comprise an activator 209, 210 for operation of the release mechanism 208, which activator 209, 210 is accessible from the outside of the connector 200 as described above.

The foregoing has described the principles, preferred embodiments, aspects and modes of operation of the present invention. However, the description should be regarded as illustrative rather than restrictive, and the invention should not be limited to the particular embodiments and aspects discussed above. The different features of the various embodiments, aspects and versions of the invention can be combined in other combinations than those explicitly described. It should therefore be appreciated that variations may be made in those embodiments and aspects by those skilled in the art without departing from the scope of the present invention as defined by the following claims.

The invention claimed is:

1. A method for preventing biofilm formation on at least one luminal surface of a catheter system, the catheter system comprising a collection vessel and a tube having a first end and a second end, wherein the first end of the tube is coupled to the collection vessel, wherein the catheter system further comprises a catheter connector coupled to the second end of the tube and connectable to a catheter, wherein the method comprises the consecutive steps of:
   connecting the catheter connector to the catheter; and
   supplying a silicon oil to an interior of the catheter connector such that the silicon oil flows directly into the tube and towards the collection vessel.

2. The method according to claim 1, wherein the method comprises the further step of:
   letting body fluid enter the catheter connector.

3. The method according to claim 1, wherein the catheter connector comprises a port providing access to the interior of the connector and the silicon oil is contained in a dispensing unit, wherein the supplying step is performed by:
   introducing the dispensing unit into the port; and
   transferring the silicon oil from the dispensing unit to the interior of the connector.

4. The method according to claim 3, wherein the dispensing unit is a pipette or a syringe.

5. The method according to claim 3, wherein the silicon oil is prefilled in the dispensing unit.

6. The method according to claim 3, wherein the dispensing unit and/or the silicon oil is sterile.

7. The method according to claim 1, wherein the catheter connector comprises a reservoir containing the silicon oil, wherein the catheter connector comprises a release mechanism releasing the silicon oil to the interior of the connector, wherein the supplying step is performed by activating the release mechanism whereby the silicon oil is released from the reservoir to the interior of the connector.

8. The method according to claim 7, wherein the release mechanism comprises an activator for operation of the release mechanism, which activator is accessible from the outside of the connector, wherein the activation of the release mechanism is performed by actuating the activator.

9. The method according to claim 7, wherein the release mechanism is activated when the catheter connector is connected to the catheter.

10. The method according to claim 7, wherein the silicon oil is prefilled in the reservoir.

11. The method according to claim 7, wherein the catheter connector and/or the silicon oil is sterile.

12. A catheter assembly for preventing biofilm formation on a luminal surface of a catheter system, wherein the catheter assembly comprises:
   a catheter connector connectable to a catheter and to a tube coupled to a collection vessel, wherein the catheter connector comprises a port providing access to the interior of the connector, and
   a dispensing unit containing a silicon oil, which dispensing unit is adapted to be introduced into the port of the connector and to supply the silicon oil to the interior of the connector such that the silicon oil flows directly into the tube and towards the collection vessel.

13. The catheter assembly according to claim 12, wherein the dispensing unit is a pipette or a syringe.

14. A catheter connector for preventing biofilm formation on a luminal surface of a catheter system, wherein the catheter connector is connectable to a catheter and to a tube coupled to a collection vessel, wherein the catheter connector comprises a reservoir containing a silicon oil and a releasing mechanism releasing the silicone oil into the interior of the connector upon activation of the releasing mechanism such that the silicon oil flows directly into the tube and towards the collection vessel.

15. The catheter connector according to claim 14, wherein the release mechanism comprises an activator for operation of the release mechanism, which activator is accessible from the outside of the connector.

* * * * *